(12) United States Patent
Fossati et al.

(10) Patent No.: US 11,241,382 B2
(45) Date of Patent: Feb. 8, 2022

(54) ADMINISTRATION REGIMEN OF COMPOSITIONS OF T4 THYROID HORMONE WITH HIGH ORAL ABSORPTION

(71) Applicant: ALTERGON SA, Lugano (CH)

(72) Inventors: Tiziano Fossati, Lugano (CH); Giuseppe Mautone, Lugano (CH); Claudia Scarsi, Lugano (CH)

(73) Assignee: ALTERGON SA, Lugano (CH)

( * ) Notice: Subject to any disclaimer, the term of this patent is extended or adjusted under 35 U.S.C. 154(b) by 117 days.

(21) Appl. No.: 16/421,373

(22) Filed: May 23, 2019

(65) Prior Publication Data

US 2020/0276112 A1 Sep. 3, 2020

Related U.S. Application Data

(60) Provisional application No. 62/834,026, filed on Apr. 15, 2019.

(30) Foreign Application Priority Data

Mar. 1, 2019 (IT) .................. 102019000003013

(51) Int. Cl.
*A61K 9/00* (2006.01)
*A61K 31/198* (2006.01)
*A61P 5/14* (2006.01)

(52) U.S. Cl.
CPC .......... *A61K 9/0053* (2013.01); *A61K 31/198* (2013.01); *A61P 5/14* (2018.01)

(58) Field of Classification Search
CPC ........ A61K 9/0053; A61K 31/198; A61P 5/14
See application file for complete search history.

(56) References Cited

U.S. PATENT DOCUMENTS

| | | | |
|---|---|---|---|
| 3,035,974 A | 5/1962 | Murray | |
| 3,128,920 A | 4/1964 | Volckening et al. | |
| 5,951,989 A | 9/1999 | Heymann | |
| 6,458,842 B1 | 10/2002 | Dickinson et al. | |
| 7,723,390 B2 | 5/2010 | Garavani et al. | |
| 9,345,772 B1* | 5/2016 | Parikh ................ | A61K 9/08 |
| 10,537,538 B2 | 1/2020 | Fossati et al. | |
| 2003/0050344 A1 | 3/2003 | Garavani et al. | |
| 2004/0266877 A1 | 12/2004 | Dickinson et al. | |
| 2005/0059574 A1 | 3/2005 | Klein et al. | |
| 2010/0197790 A1 | 8/2010 | Zoppetti et al. | |
| 2014/0073695 A1 | 3/2014 | Psarrakis et al. | |
| 2014/0179785 A1 | 6/2014 | Bellorini et al. | |
| 2018/0104204 A1 | 4/2018 | Fossati et al. | |
| 2018/0353432 A1 | 12/2018 | Carucci et al. | |

FOREIGN PATENT DOCUMENTS

| | | |
|---|---|---|
| EP | 1291021 A2 | 3/2003 |
| GB | 2191695 A | 12/1987 |
| WO | WO 2007/077252 A | 7/2007 |
| WO | WO 2010/086030 A1 | 8/2010 |
| WO | WO 2012/120338 A1 | 9/2012 |
| WO | WO 2013/072304 A1 | 5/2013 |
| WO | WO 2016/137969 A2 | 9/2016 |
| WO | WO 2018/073209 A1 | 4/2018 |

OTHER PUBLICATIONS

Vita, R., et al.The administration of I-thyroxine as soft gel capsule or liquid solution. Expert Opinion on Drug Delivery, 11:7, 1103-1111. 2014 (Year: 2014).*
Vita, R., et al. A novel formulation of L-thyroxine (L-T4) reduces the problem of L-T4 malabsorption by coffee observed with traditional tablet formulations. Endocrine. vol. 43, p. 154-160. 2013 (Year: 2013).*
Bhatnagar, S. Calories in Black Coffee: How it Helps to Shed Extra Kilos, https://food.ndtv.com/food-drinks/calories-in-black-coffee-how-it-helps-to-shed-extra-kilos-1866361 Jun. 12, 2018 (Year: 2018).*
Mercury Pharma , Eltroxin® 25 micrograms/50 micrograms /100 micrograms per 5 ml Oral Solution, pp. 1-2, Mar. 2012.*
Advanz Pharma, Levothyroxine 50 micrograms per 5 ml Oral Solution, pp. 1-7, Jun. 21, 2018.*
Boulton, D. et al., Stability of an Extemporaneously Compounded Levothyroxine Sodium Oral Liquid, American journal of Health-System Pharmacy, May 15, 1996, 53(10), pp. 1157-1161.
European Patent Office, Extended European Search Report, EP Patent Application No. 16194294.1, dated Mar. 29, 2017, seven pages.
Jonklaas, J. et al., "Guidelines for the Treatment of Hypothyroidism: Prepared by the American Thyroid Association Task Force on Thyroid Hormone Replacement," Thyroid, 24(12), Dec. 12, 2014, pp. 1670-1751.
Linnoila, M. et al., "Drug interactions with alcohol," Drugs, vol. 18, 1979, p. 299-311.
PCT International Search Report and Written Opinion, PCT Application No. PCT/EP2017/076412, dated Feb. 21, 2018, ten pages.
Won, C., "Kinetics of Degradation of Levothyroxine in Aqueous Solution and in Solid State," Pharmaceutical Research 9(1), Jan. 1992, pp. 131-137.
PCT International Search Report and Written Opinion, PCT Application No. PCT/EP2020/054873, dated Apr. 29, 2020, 12 pages.
Scavone, C. et al., "Medication adherence and the use of new pharmaceutical formulations: the case of levothyroxine," Minerva Endocrinologica, 41(2), Jun. 2016, pp. 279-289.
United States Office Action, U.S. Appl. No. 16/697,924, dated Aug. 4, 2020, eight pages.
Anonymous, "Highlights of Prescribing Information," Dec. 2017, pp. 1-15 [Online] [Retrieved from the Internet] <URL: https://www.accessdata.fda.gov/drugsatfda_Docs/label/2017/021924s013161.pdf>.

(Continued)

*Primary Examiner* — Ruixiang Li
(74) *Attorney, Agent, or Firm* — Fenwick & West LLP

(57) ABSTRACT

New administration regimens of the T4 thyroid hormone are described, characterized by the use of alcohol-free, water-glycerol solutions of said hormone, administered at short temporal distance, i.e. within less than 30 minutes, typically between 15 and less than 30 minutes, from the closest consumed meal.

20 Claims, No Drawings

(56) References Cited

OTHER PUBLICATIONS

Anonymous, "Highlights of Prescribing Information: These highlights do not include all the information needed to use TIROSINT-SOL safely and effectively. See full prescribing information for TIROSINT-SOL," Dec. 2016, pp. 1-19, [Online] [Retrieved from the Internet] <URL https://www.accessdata.fda.gov/drugsatfda_docs/label/2016/206977s000lbl.pdf>.

Cappelli, C. et al., "Thyroid Hormone Profile in Patients Ingesting Soft Gel Capsule or Liquid Levothyroxine Formulations with Breakfast," International Journal of Endocrinology, vol. 2016, Article ID 9043450, May 30, 2016, pp. 1-5.

Italian Patent and Trademark Office, Search Report and Opinion, IT Patent Application No. 102019000003013, dated Nov. 6, 2019, nine pages.

Morelli, S. et al., "Timing of breakfast does not influence therapeutic efficacy of liquid levothyroxine formulation," Endocrine, vol. 52, Nov. 4, 2015, pp. 571-578.

Biondi, B. et al., "Treatment with Thyroid Hormone," Endocrine Reviews 35(3), Jun. 2014, pp. 433-512.

Brancato, D. et al., "Comparison of TSH Levels with Liquid Formulation Versus Tablet Formulations of Levothyroxine in the Treatment of Adult Hypothyroidism," Endocrine Practice, vol. 20, No. 7, Jul. 2014, pp. 657-662.

Cappelli, C. et al., "Oral liquid levothyroxine treatment at breakfast: a mistake?," European Journal of Endocrinology 170(1), Nov. 22, 2013, pp. 95-99.

Peroni, E. et al., "Congenital Hypothyroidism Treatment in Infants: A Comparative Study between Liquid and Tablet Formulations of Levothyroxine," Hormone Research in Pediatrics, vol. 81, Nov. 12, 2013, pp. 50-54.

Pirola, I. et al., "Oral Liquid L-Thyroxine (L-T4) May Be Better Absorbed Compared to L-T4 Tablets Following Bariatric Surgery," Obesity Surgery, vol. 23, Jul. 4, 2013, pp. 1493-1496.

U.S. Appl. No. 17/434,715, filed Aug. 27, 2021, Inventors Tiziano Fossati, Giuseppe Mautone, Claudia Scarsi (copy not enclosed).

Vita, R. et al., "A Novel Formulation of Levothyroxine (Oral Solution) is Resistant to the Levothyroxine Malabsorption Induced by Proton-Pump Inhibitors (PPI)," $83^{rd}$ Annual Meeting of the American Thyroid Association, Oct. 2013, Poster 162 Abstract, pp. A-71.

Yue, C.S. et al., "Pharmacokinetics and Potential Advantages of a New Oral Solution of Levothyroxine vs. other Available Dosage Forms," Arzneimittelforschung, Nov. 15, 2012, pp. 631-636.

\* cited by examiner

ADMINISTRATION REGIMEN OF COMPOSITIONS OF T4 THYROID HORMONE WITH HIGH ORAL ABSORPTION

1. CROSS-REFERENCE TO RELATED APPLICATIONS

This application claims priority to U.S. provisional application No. 62/834,026, filed Apr. 15, 2019, and Italian application no. IT102019000003013, filed Mar. 1, 2019, the disclosures of which are incorporated herein by reference in their entireties.

2. BACKGROUND OF THE INVENTION

The T4 thyroid hormone (levothyroxine or tetraiodothyronine) is secreted by the follicular cells of the thyroid as a response to the pituitary gland hormone TSH, whose production is in turn regulated by the hypothalamic hormone TRH. The thyroid also secretes the T3 hormone (liothyronine or triiodothyronine); however, most of the T3 in the human body results from the metabolic conversion of T4 into T3, which is performed outside of the thyroid. Thyroid hormones are essential for normal body development of children and for the maturation of various organs, in particular the skeleton, and regulates metabolic activity in the adult, influencing the function of every organ and tissue. In particular, the hormones T3/T4 increase oxygen consumption at rest, increasing basal metabolism, body temperature and daily caloric needs. They further regulate carbohydrate metabolism, promoting glycogenolysis and gluconeogenesis and increase the activity of the enzymes involved in glucose oxidation. T3/T4 thyroid hormones are involved in lipolysis and in lipogenesis, regulate protein synthesis, exert a trophic effect on the muscle and influence the cardiovascular system. They are further essential for heart function: they increase myocardial contractibility (positive inotropic effect), heart rate (positive chronotropic effect) and venous return to the heart.

Pharmaceutical compositions of thyroid hormones are commonly used for the treatment or the prevention of diseases associated with thyroid hormone deficiency. The treatment typically continues throughout the patient's life and the posology (dose and frequency of administration) should be personalized according to the response of the patient. Thyroid hormones are conveniently orally administered. The use of T4 hormone is generally preferred to the use of T3. Administration is preferably oral. The most commonly used dosage form is an oral tablet. However, oral solutions have also been developed. For example, patent application WO2018/073209 describes an alcohol-free oral solution of T4 thyroid hormone, with high stability, i.e. being protected against the undesired conversion of T4 into T3. In another example, patent application WO2013/072304 describes compositions of T4 thyroid hormone in a water-alcohol-glycerol solution, for oral administration; the presence of alcohol, beside facilitating hormone dissolution and ensuring a good general stability, contributes to the absorption of the composition after oral administration. It is in fact known that small ethanol amounts accelerate the bioavailability of drugs enhancing their dissolution, stimulating gastrointestinal bloodstream and inhibiting metabolism of first-pass effect (*Drugs*, 18, 1979, p. 299-311); the same publication also mentions that small amounts of ethanol increase acid secretion by stomach and it is further known (e.g. from *Pharmaceutical Research*, 9(1), 1992, p 131-1378) that solubility of T4 hormone is maximized under hyperacidity conditions.

The selection of the correct dose is a critical aspect of thyroid hormonal treatments: under dosing results in low response, while an excessive dose can cause toxic hyperthyroidism symptoms such as tachycardia, sweating, weight loss, nervousness, diarrhea, bone resorption due to activation of osteoclasts and cardiac problems. It is therefore important for patients to rely on formulations which are reliable in terms of dose accuracy. A quantitative absorption of the administered dose is particularly desired and is important in the case of T4 hormone: in fact, various studies report a malabsorption of T4 hormone caused by the presence of food in the gastrointestinal tract; for example, a reduction of the gastric acidity as it is observed during digestion is considered to contribute to the malabsorption of T4 when administered close to the meal; further, considering that T4 is normally administered at the beginning of the day, other studies investigated the effect on the absorption of T4 by foodstuffs which are commonly assumed with breakfast: in particular coffee turned out to be undesirably active in sequestering T4 contained in the stomach, reducing its absorption into circulation (for a review of field studies, see *Thyroid*, 24(12), 2014, p. 1670 et seq.).

Based on the above-mentioned studies, oral formulations of T4 are recommended in therapy for administration before meals and distant from them. Such administration regimens are unsuitable for the average patient, since they need a postponement of breakfast time or, alternatively, an early awakening in order not to delay breakfast; such drawbacks are worsened by the fact that T4 administration is typically chronic, so the patient is exposed to a standing interference with his/her daily routine. The uncomfortable administration regimen entails in turn compliance problems, with possible therapy interruption and reduction/loss of therapeutic effect. To date, the study of T4 formulations independent from the food regimen of the patient is substantially unexplored and there are no examples of simple T4 formulations, in particular free from additives stimulating absorption, which have low dependence from the food content of the gastrointestinal tract.

3. SUMMARY OF THE INVENTION

It has been now surprisingly observed that some pharmaceutical compositions of T4 hormone for oral administration hereinafter described, with a simple formulation, show a significant independence from the food regimen of the patient and can be administered substantially independently of the meals, i.e. the fact of being administered close to the meal does not cause a significant decrease of gastrointestinal absorption of T4. It is thereby possible to administer the formulation at shortened time intervals from the closest meal, typically within less than 30 minutes of temporal distance, e.g. between 15 and less than 30 minutes from said meal. Typically, the present T4 compositions are administered in the morning, within the above-mentioned temporal distances from breakfast. The interference between nutrition and T4 administration is thus significantly reduced and higher and reproducible blood levels of T4 are obtained, i.e. less influenced by the food cycle of the patient. Further, the problem of the uncomfortable administration regimen recommended till now for oral T4 formulations is solved, thereby obtaining an improvement in compliance and ensuring a better therapeutic effect.

4. DETAILED DESCRIPTION OF THE INVENTION

An object of the invention is a new mode (regimen) of administration of the T4 thyroid hormone, highly effective from the point of view of the absorption into circulation of said hormone, wherein an alcohol-free, water-glycerol solution of T4 thyroid hormone is administered in the treatment or prevention of a disease caused by thyroid hormone deficiency; said administration regimen is characterized in that the administration of the solution is performed within particularly short time intervals with respect to the closest meal consumed by the patient, typically at a temporal distance of less than 30 minutes, e.g. between 15 and 30 minutes from said meal. The administration of the present solution of T4 thyroid hormone can be performed before or after the meal at issue; preferably it occurs before the meal. The term "consumed meal" is herein meant in the broad sense to indicate a meal which can be indifferently consumed before or after administration of the present solution of T4 thyroid hormone, within the above-mentioned temporal distances. The meal can be any meal which is part of the normal food routine, i.e. breakfast, brunch, lunch, happy hour, dinner, etc.; considering that T4 administration occurs preferably early in the morning, the meal at issue will preferably be breakfast. As regards the qualitative and quantitative content of the meal, there are no binding limitations: it is however preferable that the meal at issue has a moderate nutritional content, as it can be generally defined as "light meal". The nutritionist expert is normally able to select a light meal, with reference to the type and amount of foodstuffs which compose it, in particular the amount of contained fats; a definition of light meal, useful according to the invention, is that of a meal with a caloric content lower than 750 calories, preferably lower than 500 calories, more preferably lower than 300 calories, independently of the type of foodstuffs which compose it. A mean continental breakfast (comprising one among milk/coffee/tea, and further fibers, yogurt, snack food in small amount), is ideally a "light meal" according to the present invention.

Based on the principles explained above, the invention can be defined as a pharmaceutical composition comprising T4 thyroid hormone in an alcohol-free, water-glycerol solution, for use in the treatment or prevention of a disease associated with deficiency of one or more thyroid hormones, characterized in that said composition is administered within less than 30 minutes, e.g. between 15 and less than 30 minutes from the closest consumed meal.

The invention can be equally defined as the use of an alcohol-free, water-glycerol solution of T4 thyroid hormone in the preparation of a medicament for the treatment and/or prevention of diseases caused by a reduced production of one or more thyroid hormones, wherein said medicament is administered (i.e. is part of an administration regimen in which said administration occurs) within less than 30 minutes, e.g. between 15 minutes and less than 30 minutes from the closest consumed meal.

The invention can be equally defined as a method for the treatment and/or prevention of diseases caused by a reduced production of one or more thyroid hormones, characterized by administering an alcohol-free, water-glycerol solution of T4 thyroid hormone within less than 30 minutes, e.g. between 15 and less than 30 minutes from the closest consumed meal.

The invention can be equally defined as the treatment, by administration of an alcohol-free, water-glycerol solution of T4 thyroid hormone, of a subgroup of patients suffering from diseases caused by a reduced production of one or more thyroid hormones, said patients being selected among those who have consumed (or will consume) the closest meal within less than 30 minutes, e.g. between 15 minutes and less than 30 minutes from said administration.

In all above-mentioned forms, the reference time points for calculating the above-mentioned temporal distance are those when: (a) the oral dosage form is ingested, namely it contacted the mouth of the patient and (b) the closest meal has started.

The water-glycerol solution used in the present invention comprises water and glycerol in widely varying amounts; water is not necessarily added, as it can be the one originally comprised in commercial glycerol (the latter is indeed provided with a titer of 85%, i.e. at the concentration of 85% w/w in water); other values in w/w concentration of glycerol in water can be used within the scope of the present invention; for example 40%, 45%, 50%, 55%, 60%, 65%, 70%, 75%, 80%, 85%, 90%, 95%, 99% and any ranges among them.

In the present solutions, the weight ratio between T4 hormone and glycerol [herein meant as pure substance, namely without considering its aqueous component] is generally between 0.002:1000 and 2.5:1000 (i.e. from 2 to 2500 ppm). Preferably, the present water-glycerol solutions are formulated and packaged as single dosage units (single-dose package); in this case, the suitable dose unit will typically contain from 5 to 1000 µg (or preferably from 10 to 500 µg) of T4 hormone.

The term "alcohol-free", associated with the present solutions of T4 thyroid hormone, means that the solution is free from low molecular weight alcohols; the term "low molecular weight alcohols" means an alkanol with molecular weight lower than 80 Dalton: e.g. methanol, ethanol, propanol, propanediol, isopropanol and similar alcohols; the term "alcohol-free" remains thus compatible with the presence of glycerol in the solution (whose molecular weight is 92.1 Dalton). Examples of water-glycerol solutions in accordance with the above-mentioned parameters and preferably usable in the context of the present invention are described in the co-pending application WO2018/073209 in the name of the Applicant, herein incorporated by reference. In the context of the present invention it is particularly significant that, even if the water-glycerol solutions at issue are free from ethanol or similar alcohols which are able to promote the absorption of the active ingredient through the mucosae, and considering the known difficulty of the T4 hormone when orally administered to be absorbed closely to the meals, the water-glycerol solutions at issue can cause a substantially unchanged absorption of T4 at considerably shortened time intervals from the last meal, e.g. of the order of about 20 minutes.

Although characterized by the presence of T4 thyroid hormone as main active ingredient, the present compositions can optionally contain other active ingredients, in particular further active ingredients useful for the treatment of diseases caused by the deficiency of thyroid hormone and/or related symptomatologies. A typical further active ingredient of this type can be the T3 thyroid hormone: the latter can be intentionally added or be contained in traces (e.g. as by-product from conversion from T4 into T3); in the latter case, T3 amount will typically be very low since the present water-glycerol compositions have a high stability expressed as reduced conversion of T4 hormone into T3 hormone.

Further optional ingredients of the present solutions are those that can be commonly used in the formulation of solutions of active ingredients for oral administration. They can be chosen by the pharmaceutical formulator based on known teachings. It is however to be noted that the high stability of the present alcohol-free T4-water-glycerol solutions makes it advantageously not essential to introduce stabilizers (for example pH-adjusting agents, buffers, chelating agents, etc.); when so formulated, the compositions of the invention entail the further advantage of avoiding unnecessary administration of additives to the patient and reducing the complexity/cost of the final medicament.

The present solutions can be provided to the user in conveniently packaged form. A wide range of choice is allowed with respect to the type of packaging and material used for it. An advantageous mode of packaging is represented by squeezable single-dose containers; in particular, as described in WO2018/073209, multicomponent laminated containers made of layers of polyethylene, ethylene vinyl alcohol copolymer resins, polyvinyl chloride, polyvinylidene chloride, polyvinyl acetate, fluorinated-chlorinated resins, ionomer resins, cyclic olefin copolymers, polyamide, polystyrene, polycarbonate, laminated metals, paper, obtaining containers with an ideal squeezing degree, so as to ensure complete discharge of the dose of solution by manual compression of the container, associated with an excellent protection of the solution; moreover, as it is also shown in WO2018/073209, said protection can be increased using a container as described above, in association to a secondary container which contains it: said secondary container can be e.g. a sachet made by lamination of different materials such as e.g. polyethylene, polyethylene terephthalate, ionomer resins, aluminum, paper, ethylene vinyl alcohol copolymer resins, fluorinated-chlorinated resins, etc.

The present invention is now described by way of the following non-limiting examples.

5. EXAMPLES

A randomized, open-label, pharmacokinetic study, with crossed design, compared the oral levothyroxine solution according to the present invention administered as 600 mcg single dose 20 minutes before breakfast or in total fasted conditions (i.e., fasting from 10 hours before to 4 hours after levothyroxine administration) in 12 healthy volunteers. The study provided the following results.

TABLE 1

Summary of the pharmacokinetic parameters calculated for serum levothyroxine and adjusted for basal levels

| Parameter (unit) | N | oral solution of levothyroxine administered in total fasted conditions (A) | | | N | oral solution of levothyroxine administered 20 minutes before breakfast (B) | | |
|---|---|---|---|---|---|---|---|---|
| | | Mean | SD | CV % | | Mean | SD | CV % |
| $AUC_{0-48}$ (h*ng/mL) | 12 | 1615.65 | 317.63 | 19.66 | 12 | 1365.20 | 386.47 | 28.31 |
| $C_{max}$ (ng/mL) | 12 | 65.47 | 11.21 | 17.13 | 12 | 55.10 | 11.56 | 20.98 |
| Parameter (unit) | N | Median | Min | Max | N | Median | Min | Max |
| $T_{max}$ (h) | 12 | 1.747 | 1.494 | 2.998 | 12 | 1.495 | 0.504 | 3.998 | abbreviations
N: number of observations; SD: Standard deviation; CV: Coefficient of variation; Min: Minimum; Max: Maximum; $C_{max}$: maximum observed concentration; $AUC_{0-48}$: Area under the curve concentration-time from time zero to time of the last measurable concentration; $T_{max}$: time of $C_{max}$ observed
treatment conditions
Treatment A: oral solution of levothyroxine (600 μg) administered in total fasted conditions. Treatment B: oral solution of levothyroxine (600 μg) administered 20 minutes before breakfast.

TABLE 2

Geometric least squares mean ratio (B/A) for pharmacokinetic parameters calculated for serum levothyroxine and adjusted for basal levels

| | Geometric LSM | | |
|---|---|---|---|
| Parameter (unit) | Treatment A | Treatment B | Ratio[1] (%) |
| $AUC_{0-48}$ (h*ng/mL) | 1568.86 | 1315.35 | 83.84 |
| $C_{max}$ (ng/mL) | 64.09 | 54.11 | 84.43 |

[1]Calculated using the least squares means according to the formula: $\exp^{(DIFFERENCE)} * 100$.
abbreviations
LSM: least squares mean; $C_{max}$: maximum observed concentration; $AUC_{0-48}$: Area under the curve concentration-time from time zero to time of the last measurable concentration.
treatment conditions
Treatment A: oral solution of levothyroxine (600 μg) administered in total fasted conditions.
Treatment B: oral solution of levothyroxine (600 μg) administered 20 minutes before breakfast.

The data provided above show that the rate and extent of the absorption of the oral solution of levothyroxine administered 20 minutes before breakfast remain higher than 80% with respect to those of the oral solution of levothyroxine administered in total fasted conditions: it is a very moderate variation, also considering the wide temporal difference of administration of the closest meal in the case of treatment A or B. It is therefore deduced that the bioavailability of the oral solution of levothyroxine according to the present invention is not influenced in a clinically significant manner by the meal ingestion.

What is claimed is:

1. A method of treating a disease associated with deficiency of one or more thyroid hormones in a patient in need thereof, comprising:
   administering an effective amount of an oral solution pharmaceutical composition comprising T4 thyroid hormone in an alcohol-free, water-glycerol solution,
   wherein said composition is administered within a temporal distance of less than 30 minutes from the closest meal consumed by the patient.

2. The method of claim 1, wherein said composition is administered at a temporal distance between 15 minutes and less than 30 minutes from said meal.

3. The method of claim 2, wherein said composition is administered at a temporal distance between 15 minutes and less than 30 minutes before said meal.

4. The method of claim 3, wherein said meal is breakfast.

5. The method of claim 3, wherein said meal provides fewer than 750 calories.

6. The method of claim 3, wherein said water-glycerol solution has a w/w concentration of glycerol in water between 40 and 99%.

7. The method of claim 3, wherein said water-glycerol solution is in the form of a dosage unit, comprising 5 to 1000 µg T4 thyroid hormone.

8. The method of claim 3, wherein said water-glycerol solution is in the form of a dosage unit, comprising 10 to 500 µg T4 thyroid hormone.

9. The method of claim 3, wherein said T4 thyroid hormone is contained in an amount by weight between 2 and 2500 ppm with respect to glycerol.

10. The method of claim 3, wherein said composition is free from stabilizing agents.

11. The method of claim 1, wherein said composition is administered at a temporal distance between 15 minutes and less than 30 minutes before said meal.

12. The method of claim 11, wherein said meal is breakfast.

13. The method of claim 1, wherein said meal provides fewer than 750 calories.

14. The method of claim 1, wherein said water-glycerol solution has a w/w concentration of glycerol in water between 40 and 99%.

15. The method of claim 1, wherein said water-glycerol solution is in the form of a dosage unit, comprising 5 to 1000 µg T4 thyroid hormone.

16. The method of claim 1, wherein said water-glycerol solution is in the form of a dosage unit, comprising 10 to 500 µg T4 thyroid hormone.

17. The method of claim 1, wherein said T4 thyroid hormone is contained in an amount by weight between 2 and 2500 ppm with respect to glycerol.

18. The method of claim 1, wherein said composition is free from stabilizing agents.

19. The method of claim 1, wherein the oral solution pharmaceutical composition consists essentially of T4 thyroid hormone in an alcohol-free solution of water and glycerol, and optionally T3 thyroid hormone.

20. The method of claim 1, wherein the oral solution pharmaceutical composition is administered from a single dose container.

* * * * *